United States Patent [19]

Sommer

[11] Patent Number: 4,984,889

[45] Date of Patent: Jan. 15, 1991

[54] PARTICLE SIZE MEASURING SYSTEM WITH COINCIDENCE DETECTION

[75] Inventor: Holger T. Sommer, Greenbelt, Md.

[73] Assignee: Pacific Scientific Company, Newport Beach, Calif.

[21] Appl. No.: 321,409

[22] Filed: Mar. 10, 1989

[51] Int. Cl.$^5$ .................. G01N 15/14; G01N 21/53
[52] U.S. Cl. ................................. 356/336; 356/339
[58] Field of Search ............... 356/336, 338, 339, 342

[56] References Cited

U.S. PATENT DOCUMENTS

| | | | |
|---|---|---|---|
| 4,095,775 | 6/1978 | Hotham | 356/102 |
| 4,303,342 | 12/1981 | Takahashi | 356/427 |
| 4,675,520 | 6/1987 | Harrsen et al. | 250/222.2 |
| 4,683,579 | 7/1987 | Wardlaw | 377/11 |
| 4,746,215 | 5/1988 | Gross | 356/339 |
| 4,798,465 | 1/1989 | Knollenberg | 356/336 |

FOREIGN PATENT DOCUMENTS 61-38447 2/1986 Japan .

OTHER PUBLICATIONS

Glantschnig et al., "Light Scattering Device for Sizing and Velocimetry of Large Droplets Utilizing a Ring-Shaped Laser Beam", *Applied Optics*, vol. 21 No. 13, pp. 2456-2460, Jul. 1982.

Primary Examiner—Davis L. Willis
Assistant Examiner—Matthew W. Koren
Attorney, Agent, or Firm—Lane, Aitken & McCann

[57] ABSTRACT

In a particle detector, a stream entraining particles to be measured is passed through a laser beam. Light scattered in two different directions from the laser beam by particles are detected by photodetectors and a coincidence circuit detects simultaneous pulses generated by both photodetectors to discriminate against noise and to disable the integration function in baseline control circuits for preamplifiers amplifying the output signals from the photodetectors. In an alternative embodiment arrays of photodetectors are arranged to detect light scattered in different directions from the sample stream. Optics are provided to focus light scattered from different positions in the sample stream upon different photodetectors in each array so that simultaneous particles in the sample stream can be detected.

5 Claims, 2 Drawing Sheets

PARTICLE SIZE MEASURING SYSTEM WITH COINCIDENCE DETECTION

This invention relates to size measurement of particles entrained in a fluid stream and more particularly to a measuring system of the type which measures particle sizes by the characteristics of pulses generated by photodetectors in response to light scattered from particles passing through a beam of light.

Systems for measuring sizes of particles by detecting scattered light from the particles as they pass through a beam of light are known. A detecting cell for detecting particles entrained in an air or gas stream for such an instrument is disclosed in U.S. Pat. No. 4,746,215 issued May 24, 1988, invented by Kenneth P. Gross and assigned to the assignee of this application. In the system as disclosed in this patent, a gas stream entraining the particles to be measured passes through a laser beam in an external cavity of the laser. Light scattered by particles passing through the laser beam is detected to detect the presence of particles.

SUMMARY OF THE INVENTION

The ability of the systems of the prior art to detect small particles depends upon their ability to distinguish the pulses generated by the small particles from noise. In accordance with the present invention, the capability of the system to distinguish pulses caused by small particles from noise is increased by providing optics and photodetectors to detect light scattered from the light beam in two directions and using a coincidence circuit to determine when both photodetectors simultaneously generate pulses indicating the presence of a small particle. If both photodetectors generate a pulse simultaneously, then there is a high probability that the pulses were caused by a particle and were not simultaneous noise variations in the output signals from the photodetectors. The ability of the system to distinguish low amplitude pulses caused by particles from noise enables the system to detect the presence of smaller particles than the systems of the prior art.

The prior art systems are capable of detecting only one particle at a time and whenever two particles pass through the laser beam simultaneously, they are counted as one particle. A second embodiment of the present invention provides a capability of detecting simultaneous particles passing through the laser beam. In accordance with this embodiment of the invention, two linear arrays of photodetectors are arranged on each side of the measuring cell extending parallel to the long dimension of the cross section of sample stream in the measuring cell and optics are provided to focus light scattered from different locations in the sample stream at different points on the linear photodetector arrays. As a result, light scattered from two particles passing through the laser beam simultaneously at different positions in the sample stream will cause two photocells in each array to receive the light scattered from the two particles simultaneously. Thus, the photodetectors will detect the two particles simultaneously. Coincidence detection circuitry is connected to receive the output signals from the photodetectors to detect when two corresponding photodetectors in each array produce an output pulse at the same time and the smaller pulses produced by the photodetectors are measured only when the coincidence detection circuitry indicates that two corresponding photodetectors in each array have received scattered light indicating the passing of the particle through the light beam.

DESCRIPTION OF A PREFERRED EMBODIMENT

Figure 1:
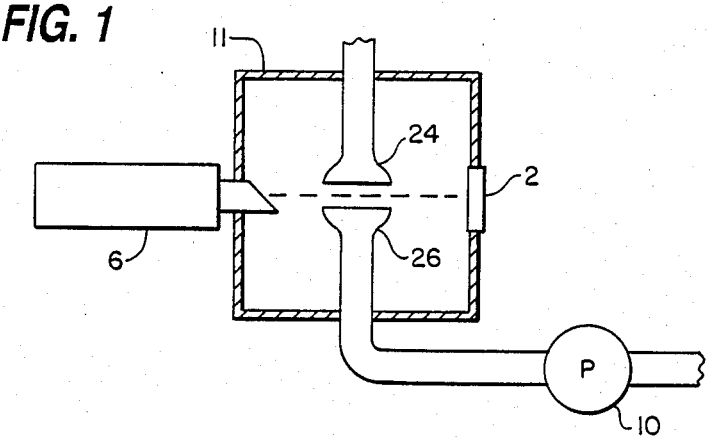
FIG. 1 schematically illustrates the measuring cell of one embodiment of the invention showing the measuring cell in section.

As shown in Fig. 1, a laser beam is generated in an external cavity of a laser defined between an end mirror 2 and a Brewster window 4 of a laser plasma tube 6, in which the laser beam is amplified. The external cavity of the laser extends across a particle detecting cell 11. A gas stream containing the particles to be measured is formed into the shape of a thin flat sheet in the particle detecting cell 11 by a nozzle 24 and is collected by an exhaust nozzle 26 and pumped from exhaust nozzle 8 by a pump 10, which controls the rate of air flow through the laser beam. The details of the nozzles generating and collecting the air stream in the external cavity are disclosed in the above mentioned Gross Pat. No. 4,746,215. The laser beam is arranged relative to the gas stream in the particle detecting cell so that it passes through the stream parallel to the long dimension of the cross section of the stream, as in the above mentioned Gross patent.

Figure 2:
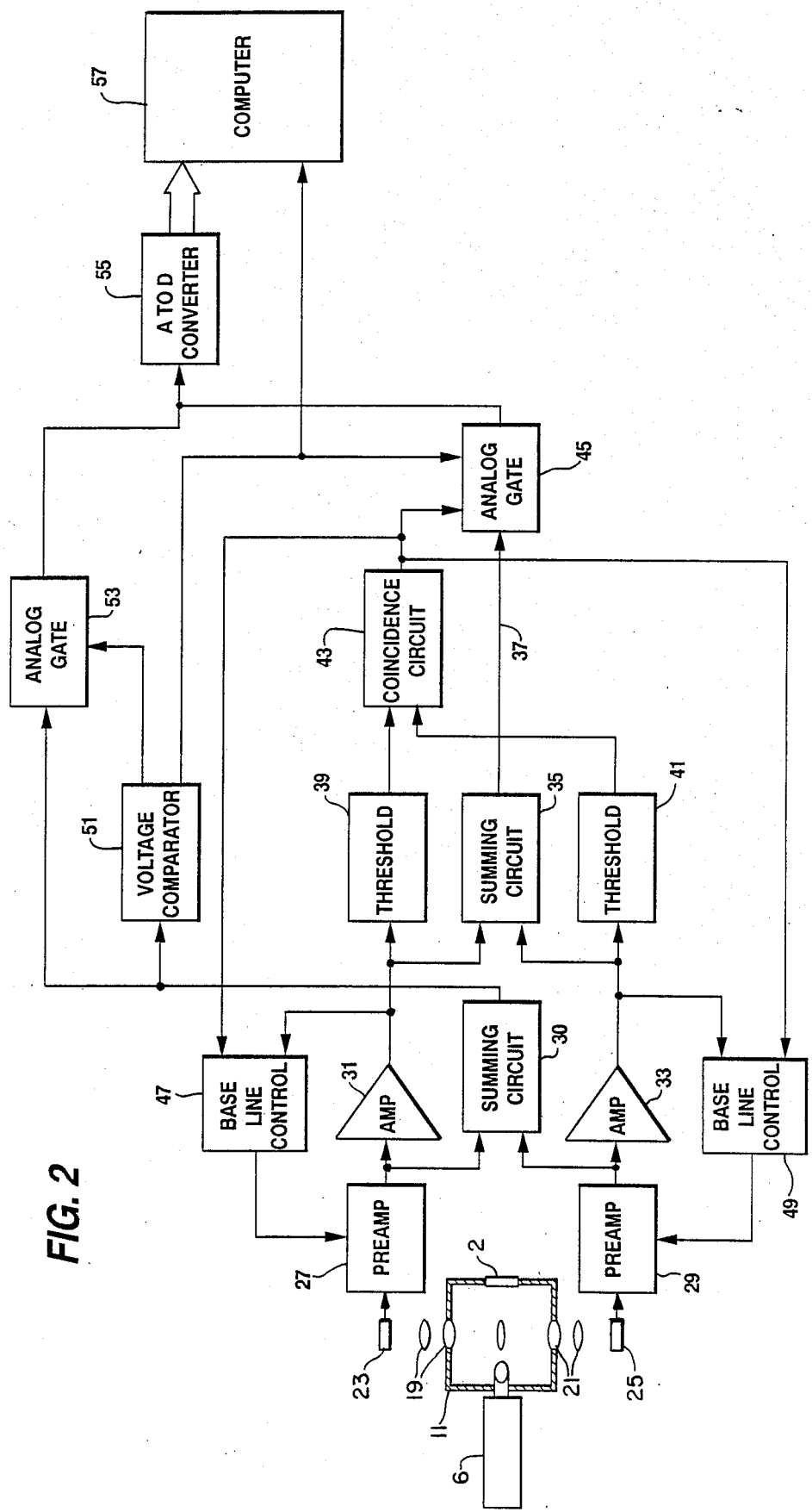
FIG. 2 is a block diagram illustrating the circuitry used with the measuring cell of FIG. 1 and showing the measuring cell in a sectional view perpendicular to the view shown in FIG. 1.

FIG. 2 includes a sectional view of the particle detecting cell taken perpendicular to the direction of flow of the sample stream 18 entraining the particulars to be measured. Any particle in the sample stream will pass through the laser beam and scatter light laterally from the laser beam. As shown in FIG. 2, laterally scattered light from the sample stream irradiated by the laser beam is focused by lens system 19 onto photodetector 23 and by lens system 21 on photodetector 25. The lens system 19 and the photodetector 23 are located on opposite side of the sample stream 18 from the lens system 21 and the photodetector 25, so that they each detect light scattered from the laser beam in opposite directions.

The output signals of the photodetectors 23 and 25 are amplified by preamplifiers 27 and 29 and then are applied to a summing circuit 30 where two signals are added together to produce a low gain analog signal on channel 32. The output signals from the preamplifiers 27 and 29 are also amplified by amplifiers 31 and 33 and then added together by summing circuit 35 to produce a high gain analog signal on channel 37. The output signals from the amplifiers 31 and 33 are also applied to threshold circuits 39 and 41, each of which generates a high level constant amplitude output signal whenever the applied input signal rises above a predetermined threshold. As a result, each of the threshold circuits 39 and 41 will produce a train of square wave pulses in response to the output pulses from the amplifiers 31 and 33 caused by particles passing through the laser beam in the cell 11. The coincidence circuit 43 detects whenever there is a coincidence in the rise times of the square wave pulses applied from the threshold detectors 39 and 41 and whenever such a coincidence occurs, the coincidence circuit 43 generates an output pulse indicating that a particle is passing through the laser beam. The output pulses of the coincidence circuit 43 have a pulse length corresponding to the length of the pulses generated by the photodetectors 23 and 25 in response to particles and are applied to base line control circuits 47 and 49, which also receive the output signals from the amplifiers 31 and 33 respectively. The base line control circuits 47 and 49 integrate the output signals from the amplifiers 31 and 33 except when receiving a pulse from the coincidence detector 43 indicating that a particle is present. The base line control circuits apply the integrated output signals as a base line input signals to the preamplifiers 27 and 29, which produce amplified outputs corresponding to the differences between the signals applied from the baselines control circuits 47 and 49 and the signals received from the photodetectors 23 and 25. In this manner, the baseline of the preamplifiers 27 and 29 are controlled in accordance with the average of output of the photodetectors 23 and 25 except when the photodetectors 23 and 25 are receiving scattered light from a particle.

The output signal from the summing circuit 30 on channel 32 is applied to a voltage comparator 51 and to an analog gate 53. When the output signal from the summing circuit 30 is above a predetermined amplitude, the voltage comparator 51 will enable the analog gate to pass the output signal from the summing circuit 30 to an analog to digital converter 55. Thus, when a pulse in the output of summing circuit 30 is large enough to cause the voltage comparator 51 to enable the analog gate 53, this output pulse will be passed to the analog to digital converter 55. The analog to digital converter is of the type which converts the peak amplitude of the applied input pulse to a digital value and applies the resulting digital value to a computer 57, which registers and responds to each received digital value in the manner described in copending application Ser. No. 144,225, filed January 15, 1988 by Kenneth Von Bargen now Pat. No. 4,842,406.

If the output signal from the summing circuit 30 is below the threshold value for the voltage comparator 51, the voltage comparator 51 will apply an enabling signal to an analog gate 45, which also receives the output pulses produced by coincidence circuit 43. The analog gate 45 is enabled by receiving simultaneously a pulse from the coincidence circuit 43 and an enabling signal from the voltage comparator 51. When the gate 45 is enabled, a pulse will be present on the high gain signal channel 37 caused by a small particle. The gate 45, when enabled, will pass the pulse on channel 37 to the analog to digital converter 55 which will convert the peak amplitude of the pulse to a digital value and apply the digital value to the computer 57. The voltage comparator 51 also applies a signal to the computer 57 to indicate to the computer 57 whether the digital value came through the analog gate 53 or the analog gate 45 so that the computer can properly scale the received digital signal.

As described in the copending application Ser. No. 144,225, the computer 57 is programmed to increment a count in its memory corresponding to the received digital value so that a count of particle sizes in each individual size range represented by a different digital value received from the analog-to-digital converter 55 is obtained. The computer 57 is also operable to display the counts of the different particle size ranges.

Figure 3:
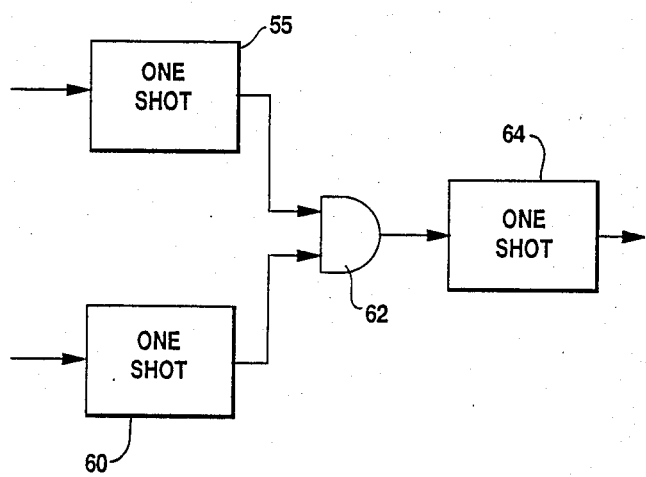
FIG. 3 is a block diagram illustrating the coincidence circuitry employed in the system of the present invention.

FIG. 3 is a block diagram illustrating the details of the coincidence circuit 43. As shown in FIG. 3, the output pulses from the threshold detectors 39 and 41 are applied to one shot multivibrators 58 and 60, which are connected to be triggered in response to the leading edges of received pulses from the threshold to detectors. The outputs from the one shot multivibrators are applied to an AND gate 62, which accordingly, will produce an output pulse whenever one of the shot multivibrators 58 and 60 is triggered to produce an output pulse at a time when the other one shot multivibrator has been triggered and still remains in its triggered state. Thus, the gate 62 will produce an output pulse when the rise time of the two output pulses from the threshold circuits 39 and 41 occur within a predetermined time interval of one another determined by the timing of the one shot multivibrators 58 and 60. This time interval is set to be a small fraction of the pulse length of the pulses generated by particles passing through the particle detecting cell 11. Any output pulse produced by the gate 62 triggers a one shot multivibrator 64, which in response to being triggered produces an output pulse length corresponding to the approximate pulse lengths of the pulses generated by the photodetectors 23 and 25 caused by particles. The output pulse from the one shot multivibrator 64 is the enabling signal applied from the coincidence circuit 43 to the analog gate 45 and to the base line control circuits 47 and 49 as shown in FIG. 2.

Figure 4:
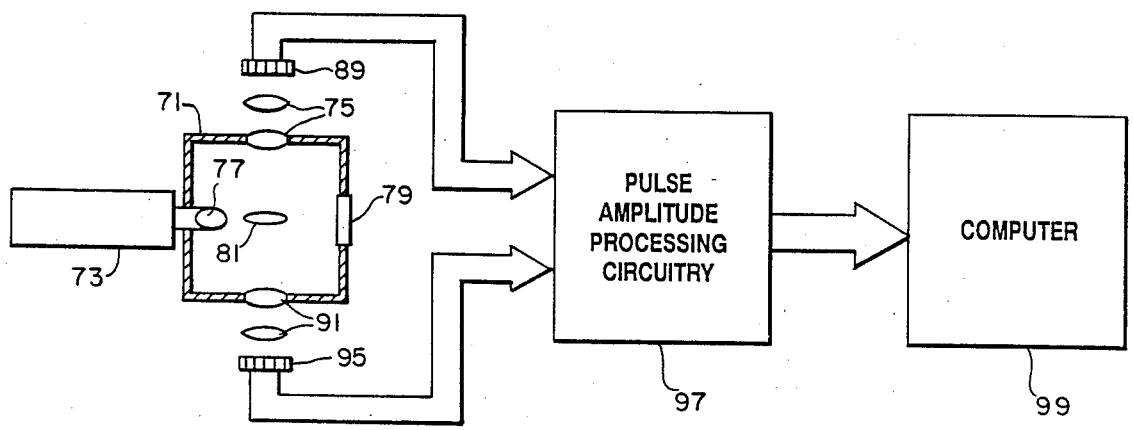
FIG. 4 schematically illustrates a second embodiment of the invention designed to detect two simultaneous pulses.

In the embodiment shown in FIG. 4, a particle measuring cell 71 is located in an external cavity of a laser comprising a plasma tube 73 having a brewster window 77 at one end. The external cavity of the laser is defined between the brewster window 77 and a mirror 79 located on the opposite side of the measuring cell from the brewster window 77. The laser beam generated by the laser will traverse the external cavity between the brewster window 77 and the mirror 79 and pass through the measuring cell, which has nozzles (not shown) like those of FIG. 1 to form a sample stream 81 of gas passing through the laser beam. The sample stream 81 is in the shape of a flat sheet with its longer dimension parallel to the laser beam. A particle passing through the laser beam in the sample stream will cause light from the laser beam to be scattered laterally from the laser beam in both directions. A first optical system comprising lenses 75 will collect the scattered light and focus an image of the source of the scattered light on a linear array of photodetectors 89 arranged parallel to the laser beam and to the long dimension of the sample stream 81. As a result, a point of light will be focused on the array 89 in a position on the array 89 corresponding to the relative location of the particle along the axis of the laser beam within the sample stream 81. As a result, particles passing through the laser beam at different locations along the laser beam will cause points of light to be focused on the array 89 at different locations along the array and if two entrained particles pass through the laser beam simultaneously at different locations, they will both generate simultaneous points of light at different locations on the array 89 and be detected by different photodetectors of the array 89. The arrangement of the lenses 75 and the array 89 is duplicated on the opposite side of the measuring cell 71 by lenses 91 and a linear array of photodetectors 95 arranged parallel to the axis of the laser beam.

As a result, light scattered in the opposite direction from that collected by lenses 75 is collected by lenses 91 and is focused on the array 95. Accordingly, when a particle passes through the laser beam in the cell 71 and scatters light, the lenses 75 will focus some of this light onto a diode in the array 89 and the lenses 91 will also focus the light scattered in the opposite direction on a corresponding diode in the array 95. If two particles pass through the laser beam in the cell 71 simultaneously, then two diodes in the array 89 will have light focused thereon and two corresponding diodes in the array 95 will also have a light thereon. The output signals from the diode and 95 are applied to a processing circuitry 97, which comprise a plurality of circuits like that shown in FIG. 2 each operating to process the signals frqm a corresponding pair of diodes to determine whether both corresponding diodes generated pulses simultaneously for small pulses and to convert the pulse amplitudes to digital values. The processing circuitry 97 applies digital signals representing pulse amplitudes to a computer 99 representing the size of each particle flowing through the cell 71 including particles that flow through the cell 71 simultaneously. The computer 99 counts each different particle size and displays the results as described above with respect to the computer 57.

In the systems as described above, because the light scattered in two different directions in the sample cell is detected and the coincidence of pulses generated by such scattered light is detected, the systems are able to distinguish smaller pulses from noise and thereby are able to detect smaller particles in the sample stream. In addition, in the embodiment employing diode arrays in the sample cell, two or more particles passing simultaneously through the laser beam can both be detected and measured.

In the above described systems, the output signals from the corresponding photodetectors are summed together and the amplitude of the pulses in the resulting signal are measured to measure the particle size. This summing is done to obtain an average pulse amplitude from the two photodetectors and thus, obtain a more accurate measurement of the particle size. However, it is not necessary to sum the signals from the two photodetectors. Instead the pulse amplitudes in the output signal from one of the two photodetectors can be measured to provide an indication of particle size while at the same time using the coincidence circuit to discriminate against noise and also to disable to the base line control when coincidence pulses are detected. These and other modifications of the above described systems may be made without departing from the spirit and scope of the invention, which is defined in the appended claims.

What is claim is:

1. A particle detection system for detecting particles entrained in a fluid stream comprising a sample cell, means to direct a sample fluid stream entraining particles to be measured through sample cell, means to generate a light beam passing through an entire cross section of said sample stream in said sample cell so that any particle entering in said stream will pass through said light beam, first and second photodetectors, means to direct light scattered in a first direction from any part of said cross section upon said first photodetector, means to direct light scattered in a second direction from any part of said cross section upon said second photodetector, and coincidence means to detect pulses occuring simultaneously in the output signals from said first photodetector and said second photodetector, and means responsive to said coincidence means detecting simultaneous pulses to measure the size of particles causing said simultaneous pulses from the amplitude of at least one of said simultaneous pulses.

2. A particle detecting system for detecting particles entrained in a fluid stream comprising a sample cell, means to direct a sample fluid stream entraining particles to be measured through said sample cell, means to generate a light beam passing through said sample stream in said sample cell, first and second photodetectors, means to direct light scattered in a first direction from said light beam in said sample cell upon said first photodetector, means to direct light scattered in a second direction from said light beam in said sample cell upon said second photodetector, coincidence means to detect pulses occurring simultaneously in the output signals from said first photodetector and said second photodetector, an amplifier connected to amplify the output signal from at least one of said photodetectors and means responsive to the output signal of said amplifier and said coincidence means to generate a base line signal varying in accordance with an integral of the output signal for said amplifier accumulated only when said coincidence means indicates no simultaneous pulses in the output signals from said photodetectors and to control the baseline of said amplifier in accordance with said baseline signal.

3. A particle detecting system for detecting particles entrained in a fluid stream comprising a sample cell, means to direct a sample fluid stream entraining particles to be measured through said sample cell, means to generate a light beam passing through sample stream in said sample cell, first and second photodetectors, means to direct light scattered in a first direction from said light beam in said sample cell upon said first photodetector, means to direct light scattered in a second direction from said light beam in said sample cell upon said second photodetector, coincidence means to detect pulses occurring simultaneously in the output signals from said first photodetector and said second photodetector, means to provide a low gain signal comprising the output signal from at least one of said photodetectors amplified with a first degree of amplification, means to provide a high gain signal comprising the output signal from at least one of said photodetectors amplified with a second degree of amplification greater than said first degree of amplification, means to measure the amplitude of the pulses in said low gain signal when the amplitude of the output signal of said photodetectors are above a predetermined threshold value and means to measure the amplitude of the pulses in said high gain signal when the amplitudes of the output pulses of said photodetectors are below said predetermined value only when said coincidence means indicates a coincidence of pulses in the output signal from said photodetectors.

4. A particle detection system for detecting particles entrained in a fluid stream comprising a sample cell, means to direct a sample fluid stream entraining particles to be measured through said sample cell, means to generate a light beam passing through said sample stream in said sample cell, an array of photodetectors, means to focus light scattered from different positions in said sample stream passing through said light beam upon different photodetectors in said array; a second array of photodetectors and means to focus light scattered from different positions in said stream where said stream passes through said light beam upon different photodetectors in said second array, said second means focusing light scattered in a different than said first mentioned means to focus light, and means to detect pulses occurring simultaneously in the output signals from correspondings photodetectors in said first mentioned array and said second array.

5. A particle detection system as recited in claim 2, wherein said means to direct a sample stream entraining particles to be measured shapes into stream into the form of a flat sheet and wherein said means to focus light focuses light from different positions along the long dimension of a cross section of said sample stream upon different photodetectors in said array.

* * * * *

UNITED STATES PATENT AND TRADEMARK OFFICE
CERTIFICATE OF CORRECTION

PATENT NO. : 4,984,889
DATED : January 15, 1991
INVENTOR(S) : Holger T. Sommer

It is certified that error appears in the above-identified patent and that said Letters Patent is hereby corrected as shown below:

Column 5, line 12, after "light", insert --focused--;

line 13, after "diode", insert --arrays 89--; and line 16, change "frqm" to --from--.

Column 7, line 4, after "different", insert --direction--;

Column 8, line 2, change the first occurrence of "into" to --said--.

Signed and Sealed this

Tenth Day of November, 1992

*Attest:*

DOUGLAS B. COMER

*Attesting Officer*   Acting Commissioner of Patents and Trademarks